United States Patent
Mamigonians et al.

(10) Patent No.: US 11,022,504 B2
(45) Date of Patent: Jun. 1, 2021

(54) DETECTING CHANGES IN ATTRIBUTES OF A HUMAN OR ANIMAL BODY

(71) Applicant: Zedsen Limited, London (GB)

(72) Inventors: Hrand Mami Mamigonians, London (GB); Aslam Sulaimalebbe, Cardiff (GB)

(73) Assignee: Zedsen Limited, London (GB)

( * ) Notice: Subject to any disclaimer, the term of this patent is extended or adjusted under 35 U.S.C. 154(b) by 0 days.

(21) Appl. No.: 16/625,241

(22) PCT Filed: Apr. 6, 2018

(86) PCT No.: PCT/GB2018/000059
§ 371 (c)(1),
(2) Date: Dec. 20, 2019

(87) PCT Pub. No.: WO2018/234727
PCT Pub. Date: Dec. 27, 2018

(65) Prior Publication Data
US 2020/0141819 A1      May 7, 2020

(30) Foreign Application Priority Data

Jun. 22, 2017 (GB) ........................... 1709962
Aug. 7, 2017 (GB) ........................... 1712643

(51) Int. Cl.
*G01L 1/14*      (2006.01)
*A61B 5/11*      (2006.01)
(Continued)

(52) U.S. Cl.
CPC ............ *G01L 1/146* (2013.01); *A61B 5/1115* (2013.01); *A61B 5/1116* (2013.01);
(Continued)

(58) Field of Classification Search
CPC ......... G01L 1/146; G01L 1/144; G01L 1/205; A61B 5/1115; A61B 5/1116; A61B 5/6892; A61B 2503/04
(Continued)

(56) References Cited

U.S. PATENT DOCUMENTS 4,014,217 A    3/1977    Lagasse et al.
8,857,247 B2   10/2014   Kjoller et al.
(Continued)

FOREIGN PATENT DOCUMENTS

| GB | 2488600 A | 9/2012 |
|---|---|---|
| WO | 2015157790 A1 | 10/2015 |
| WO | 2016086306 A1 | 9/2016 |

OTHER PUBLICATIONS

Corresponding International Patent Application No. PCT/GB2018/000059, International Search Report and Written Opinion, dated Jun. 26, 2018.
(Continued)

*Primary Examiner* — Max H Noori
(74) *Attorney, Agent, or Firm* — Cooper Legal Group, LLC

(57) ABSTRACT

Attributes of a human or animal body are detected by the generation and detection of an electric field. A laminated membrane, connected to a control circuit, is placed over an electrically conductive ground-plane. An upper-mattress is placed above this for supporting a human or animal body. To improve the response of the detector, a response-enhancement-layer of a substantially electrically non-conducting compressible-material containing electrically-conductive-particles, such as carbon particles, is located between the laminated-membrane and the upper-mattress.

15 Claims, 16 Drawing Sheets

(51) Int. Cl.
  *A61B 5/00*    (2006.01)
  *G01L 1/20*    (2006.01)
(52) U.S. Cl.
  CPC ............ *A61B 5/6892* (2013.01); *G01L 1/144* (2013.01); *G01L 1/205* (2013.01); *A61B 2503/04* (2013.01)
(58) Field of Classification Search
  USPC .................................................... 73/862.626
  See application file for complete search history.

(56) References Cited

U.S. PATENT DOCUMENTS

| | | | |
|---|---|---|---|
| 8,994,383 B2 | 3/2015 | Mamigonians | |
| 9,816,800 B2* | 11/2017 | O'Brien | ................... B32B 37/16 |
| 10,714,676 B2* | 7/2020 | Otagiri | .................... H02N 1/04 |
| 2003/0125781 A1* | 7/2003 | Dohno | ............. A63B 21/00181 |
| | | | 607/75 |
| 2005/0190068 A1 | 9/2005 | Gentry et al. | |
| 2013/0060164 A1* | 3/2013 | Fujita | ................. A61B 5/02444 |
| | | | 600/586 |
| 2017/0273599 A1* | 9/2017 | Reese | .................... G01L 1/146 |

OTHER PUBLICATIONS

Corresponding International Patent Application No. PCT/GB2018/000059, International Preliminary Report on Patentability, completed Sep. 17, 2019.

* cited by examiner

DETECTING CHANGES IN ATTRIBUTES OF A HUMAN OR ANIMAL BODY

CROSS REFERENCE TO RELATED APPLICATIONS

This application claims priority from United Kingdom patent application number 1709962.3, filed Jun. 22, 2017 and United Kingdom patent application number 1712643.4, filed Aug. 7, 2017, the entire disclosures of which are incorporated herein by reference in their entirety.

BACKGROUND OF THE INVENTION

The present invention relates to an apparatus for detecting changes in attributes of a human or animal body, of the type comprising an electrically conductive ground-plane; a laminated-membrane having electrodes connected to a control-circuit; and an upper-mattress for supporting a human or animal body, wherein said control-circuit is configured to energise and monitor selected ones of said electrodes, such that an electric field passes through said upper mattress.

The present invention also relates a method of constructing a mattress-based detection-device for a human or animal body, of the type comprising the steps of: establishing an electrically conductive ground-plane; and configuring a laminated-membrane of a detector over said ground-plane, having a plurality of electrodes for generating and monitoring electric fields.

It is known to provide detection devices that can detect changes in various attributes of human or animal bodies. Usually, when using devices of this type, the body remains in position for a relatively short period of time. Known detectors have a relatively solid construction and will tend to become uncomfortable if someone is required to sit, lie down and possibly sleep on a device for extended periods of time.

A possible solution would be to provide sufficient layers of deformable material, possibly in the form of a foam-like mattress, but in applications where attributes are being identified in response to the detection of a varying electric field, the provision of mattress like substances in this way will impede the field and make detection significantly more difficult. Furthermore, in order to extend the electric field towards and possibly through the human or animal body, it is necessary to remove an upper ground plane which in turn may reduce the signal-to-noise level of any input signals. Consequently, any further attenuation of the input signal is considered to be highly undesirable.

BRIEF SUMMARY OF THE INVENTION

According to a first aspect of the present invention, there is provided an apparatus of the aforesaid type, characterised by a response enhancement layer of a substantially electrically non-conducting compressible-material containing electrically-conductive-particles located between the laminated-membrane and the upper-mattress.

In an embodiment, the electrically-conductive-particles are particles of carbon and the compressible-material may be an expanded foam-based material.

According to a second aspect of the present invention, there is provided a method of constructing a mattress-based detection-device for a human or animal body of the aforesaid type, characterised by the steps of: deploying a response-enhancement-layer upon the laminated-membrane, wherein the response-enhancement-layer is constructed from a substantially electrically non-conducting compressible-material containing electrically-conductive-particles; and arranging an upper-mattress over said response-enhancement-layer wherein: electric fields pass through said response-enhancement-layer and said upper mattress: and detection of a human or animal body is enhanced by said response enhancement layer.

DETAILED DESCRIPTION OF THE INVENTION

FIG. 1

Figure 1:
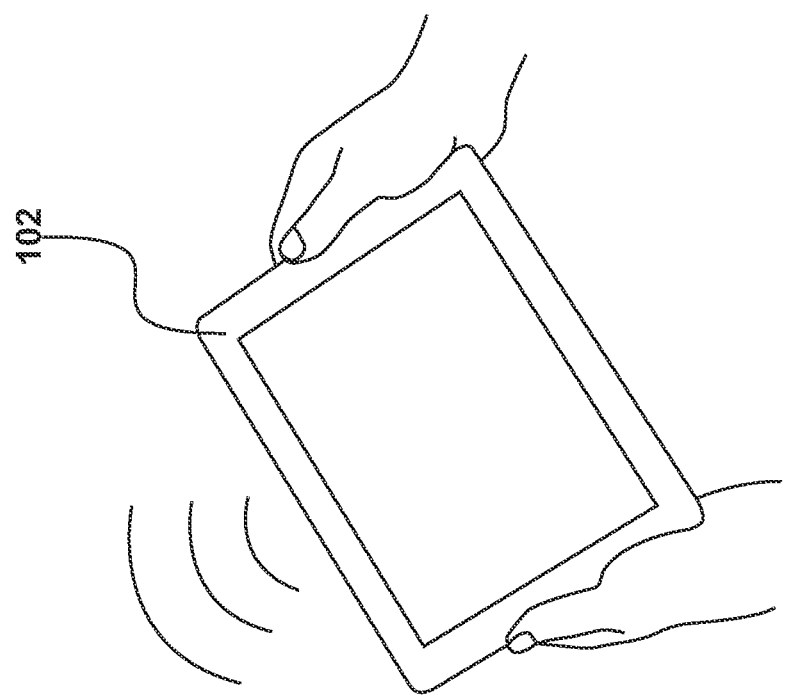
FIG. 1 shows a mattress-based detection apparatus.
Figure 1:
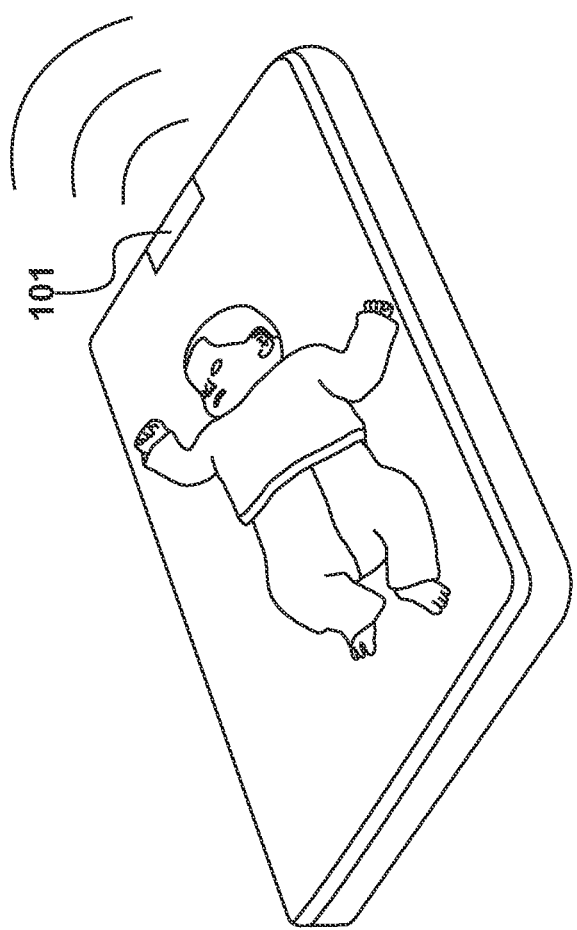

A mattress-based detection apparatus is shown in FIG. 1 that facilitates a method of detecting changes in attributes of a human or animal body sleeping on the apparatus. Output signals from a control-circuit 101 are issued to a laminated-membrane that is configured to generate an electric-field. Input signals are received in response to the electric field that vary in response to changes in these attributes. Output data is generated by the control-circuit 101 that communicates by wireless-transmission with a data-processing-system 102.

A sensor making use of a compressible layer is described in U.S. Pat. No. 8,857,247, assigned to the present applicant. This shows that a compressible layer may be used to enhance measurements of changing electric fields when the compressible layer itself is sandwiched between ground-planes. A permittivity sensor sensitive to external objects is described in U.S. Pat. No. 8,994,383. This allows sophisticated attributes to be identified due to detected changes in permittivity. However, to achieve this, the electric field must be allowed to radiate and cannot be constrained within an upper-ground-plane.

For detecting changes in attributes of a human or animal body sleeping on a mattress-based detection-device, a mattress material is required between the detector plane and the subject being detected. However, without the presence of an upper ground-plane, higher levels of noise are introduced.

The present invention mitigates this problem by providing a response-enhancement-layer located above the laminated-membrane of a substantially electrically non-conducting compressible-material containing electrically-conductive-particles. Thus, by being electrically non-conducting in the plane of the device, the response-enhancement-layer does not provide a ground-plane. As a compressible-material, it adds to the comfort requirements of the actual mattress. However, by the inclusion of electrically-conductive-particles, the response of the detector, particularly with respect to applied pressure, is enhanced, thereby increasing signal strength and improving signal-to-noise characteristics.

Thus, in its application, changes to attributes are detected in response to pressure changes that change a pressure distribution applied to the compressible-material. Changes in the pressure distribution applied to the compressible-material change a distribution of the extent to which the compressible-material is compressed. Consequently, due to the presence of the electrically-conductive-particles, the extent to which the compressible-material is compressed affects an electric-field due to relative movements of the electrically-conductive-particles.

FIG. 2

Figure 2:
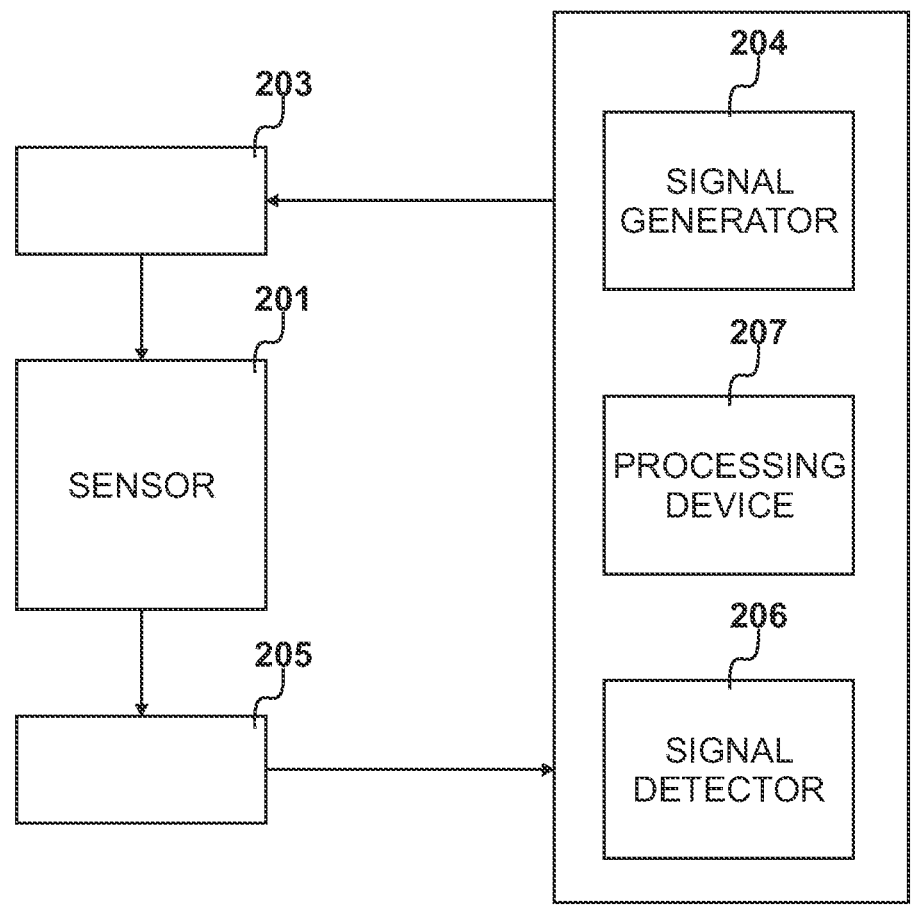
FIG. 2 shows a functional block diagram of the mattress-based detection apparatus.

A functional block diagram of the mattress-based detection apparatus is shown in FIG. 2. A sensor 201 includes multiple coplanar electrodes that experience a degree of capacitive coupling between each other. The control-circuit 101 has a signal generator 204, a signal detector 206 and a processing-device 207.

The sensor 201 is electrically connected via a pair of multiplexers to the processing-device 207. A transmitter-multiplexer 203 transmits input signals from a signal-generator 204 across selected transmitter electrodes. A demultiplexer 205 receives output signals from selected receiver electrodes and transmits the output signals into a signal-detector 206.

FIG. 3

Figure 3:
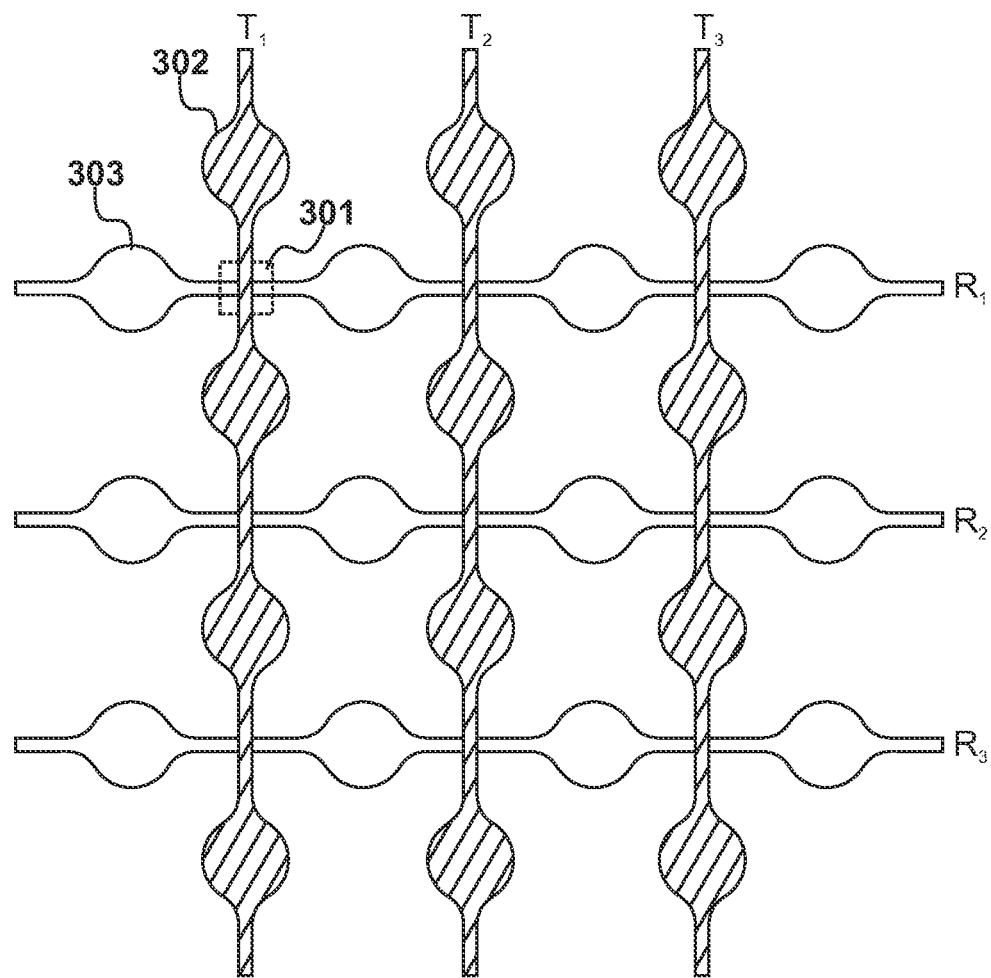
FIG. 3 shows an example of the structure of an electrically active membrane.

An example of the structure of an electrically active membrane is shown in FIG. 3. The membrane comprises a set of transmit tracks ($T_1$, $T_2$, $T_3$) separated from a set of receive tracks ($R_1$, $R_2$, $R_3$). In this example, the transmit tracks and receive tracks are orthogonal to one another. Alternatively, the transmit tracks and receive tracks may be parallel to each other or the transmit tracks may be inclined at an angle between 0 and 90 degrees to the receive tracks. Each transmit track is configured to capacitively couple to at least one receive-track on application of a voltage to the transmit track. Hence, one transmit-track may couple to one or more receive tracks.

Intersection zones, including a first-intersection-zone 301, between the transmit tracks and the receive tracks, form a parallel plate capacitor which is not affected significantly by the properties of a material placed on top or above the membrane. Hence, the track width at the intersection zones is reduced in this embodiment, to minimise the parallel plate capacitance at the intersection. In this way, the sets of transmit and receive tracks comprise enlarged active areas, including a first-enlarged-active-area 302 and a second-enlarged-active-area 303.

In operation, the transmitter multiplexer 203 directs input signals from the signal-generator 202 to transmit electrodes in sequence, while signals from one or more receive electrodes are received. The demultiplexer 205 then switches to the next receive electrode and input signals are then applied to the next sequence of selected transmit electrodes.

Thus, for example, given an array having eight electrodes in a first set arranged substantially perpendicularly to eight electrodes in a second set and being provided with input signals having a frequency of repetition $8f$, the transmit multiplexer switches across each electrode in the first set at a frequency $8f$ and the receive multiplexer switches between each electrode in the second set at a frequency f. This results in an output signal being produced that is a function of the capacitive coupling for an electrode in the first set and an electrode in the second set, giving, in this example, sixty-four data points, following processing of comparison signals by the processing-device 207.

On application of a voltage to a transmitter electrode, an electric field forms which both extends outside of the sensor array and which causes capacitive coupling to other receive electrodes in close proximity.

FIG. 4

Figure 4:
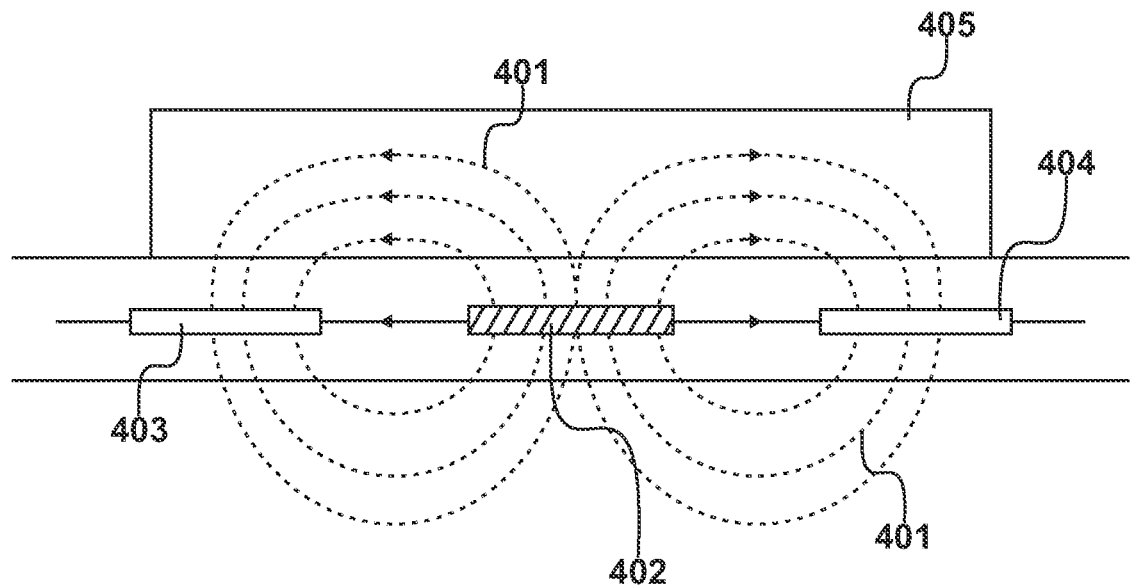
FIG. 4 illustrates the result of applying voltages to transmitter tracks.

The result of applying voltages to transmitter tracks is illustrated in FIG. 4. The cross-sectional view shows electric field lines 401 between a first-transmit-track 402 and a first-receive-track 403, and between the first-transmit-track 402 and a second-receive-track 404. A mattress-type-object 405 is positioned on top of an electrically active layer 406 that includes the electrodes 402-404. Thus, the electric-field-lines 401 from transmit tracks enter and propagate through the mattress-type-object 405. The fields are modified, due to material properties and then propagate through to the receive tracks.

The capacitive coupling between a transmit track and a nearby receive track is therefore susceptible to changes of the electrical properties of the volume through which it passes.

FIG. 5

Figure 5:
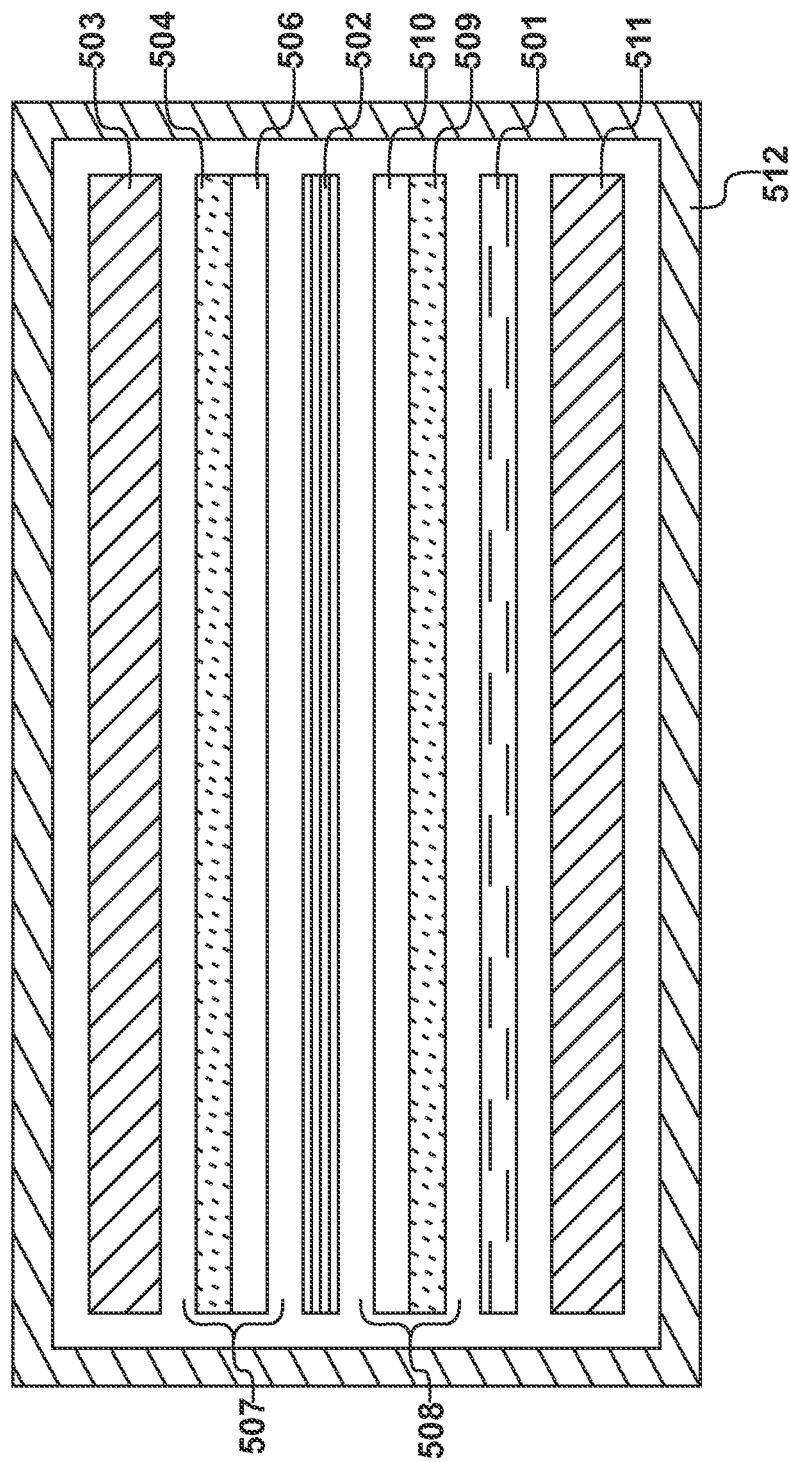
FIG. 5 shows a cross-section of the apparatus shown in FIG. 1.

A cross-section of the mattress-based detection apparatus is shown in FIG. 5. For the purpose of improving clarity, layers are shown separated in a vertical direction and it should be understood that in practice, these layers would be contacting each other.

An electrically-conductive ground-plane 501 is provided to ensure that a laminated-membrane 502 does not receive noise unnecessarily. The laminated-membrane 502 may be fabricated from polyester and an example of this material is sold commercially under the trade name Lumirror from Toray. A suitable material is identified by the commercial designation S10 and may typically have a thickness of one-hundred micrometres, one-hundred-and-twenty-five micrometres or one-hundred-and-eighty-eight micrometres.

To form the laminate, conductive tracks may be applied to the membrane by a process of screen printing conductive ink containing silver or carbon particles. A suitable example is identified by the commercial designation electrodag 479SS from Acheson. In an embodiment, the transmit tracks are printed on an opposite side of the membrane to the receive tracks but in an alternative configuration, the tracks may be printed on the same side and separated by an appropriate dielectric material.

After application of the ink, the ink may be dried in an oven operating at a temperature of ninety-three degrees Celsius, for example, and for an exposure time of fifteen minutes. After application, the ink may have a thickness of between ten and twelve micrometres and a ten-micrometre coating of a dielectric material may be applied to prevent corrosion. Thereafter, adhesive may be applied to facilitate subsequent fabrication. Furthermore, to allow transportation and further manipulation, a suitable film, possibly of paper, may be applied over the adhesive for later removal.

The laminated-membrane is connected to the control-circuit 101. An upper-mattress 503 is provided for supporting a human or animal body. A response-enhancement-layer 504 of a substantially electrically non-conducting compressible-material containing electrically-conductive-particles is located between the laminated-membrane 502 and the upper-mattress 503.

In an embodiment, the electrically-conductive-particles are particles of carbon and the compressible-material is an expanded foam-based material. In an embodiment, the compressible-material, making up the response-enhancement-layer 504, is neoprene and the particles of carbon are dispersed in this first-neoprene-layer.

In the embodiment of FIG. 5, a second-compressible-layer 506, of a material that does not contain electrically-conductive-particles, is positioned between the laminated-membrane 502 and the response-enhancement-layer 504. In an embodiment, the second-compressible-layer 506 is a second-neoprene-layer. In the embodiment of FIG. 5, the second-neoprene-layer 506 is attached to the first-neoprene-layer 504 (the response-enhancement-layer) to form a primary-neoprene-composite-layer 507.

In an embodiment, a secondary-neoprene-composite-layer 508 is located between the electrically-conductive ground-plane 501 and the laminated-membrane 502. The secondary-neoprene-composite-layer 508 comprises a third-layer 509 containing electrically-conductive-particles that is placed in contact with the electrically-conductive ground-plane 501. In addition, it includes a fourth-layer 510 that is placed in contact with the laminated-membrane 502. Thus, it should be appreciated that with the primary-neoprene-composite-layer 507, the first layer 504 containing electrically-conductive-particles is uppermost, such that the layer that does not contain particles is closest to the laminated-membrane 502. However, with the secondary-neoprene-composite-layer 508, the third layer 509 that contains electrically-conductive-particles is lowermost; again, ensuring that the fourth layer 510, that does not include electrically-conductive-particles, is closest to and possibly in contact with, the laminated-membrane 502. Alternatively, the secondary-neoprene-composite-layer could be replaced by a single secondary layer of material not containing electrically conductive particles.

To assist with the construction of the device, the primary-neoprene-composite-layer 507 and the secondary-neoprene-composite-layer 508 may both be secured to the laminated-membrane 502 to form a detector-subassembly. To complete fabrication of the apparatus 101, a lower-mattress 511 supports the ground-plane 501 and the whole assembly is then encased by a cover 512.

FIG. 6

Figure 6:
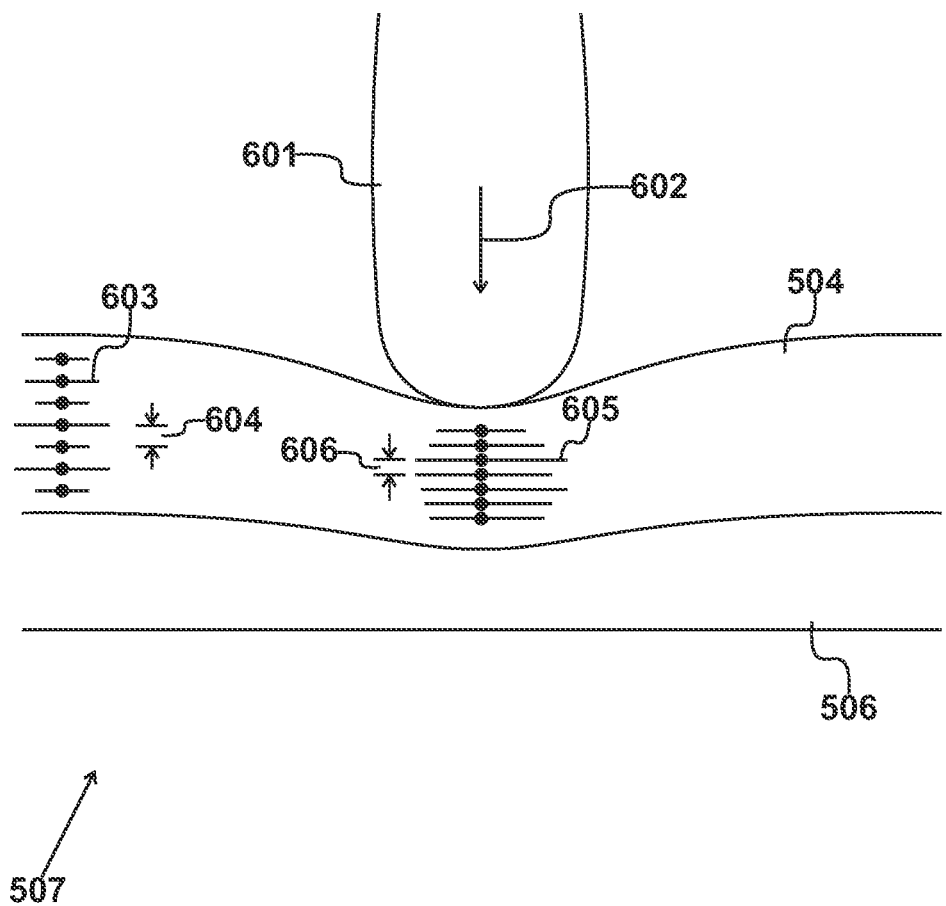
FIG. 6 shows a portion of primary-neoprene-composite-layer identified in FIG. 5.

A portion of the primary-neoprene-composite-layer 507 is illustrated in FIG. 6. This is made up of the first-neoprene-layer 504 that contains electrically-conductive particles. This is secured to the second-compressible-layer 506 that does not include electrically-conductive-particles. During assembly, it is possible to ensure that a correct orientation is achieved because a neoprene layer containing conductive carbon particles appears black, whereas the layer that does not contain carbon particles appears white. Thus, in the arrangement of FIG. 3, the black layer 504 is on top and the white layer 506 is beneath.

For the purposes of illustration, a mechanical-interaction 601 is illustrated that applies pressure in the direction of an arrow 602. This causes the primary-neoprene-composite-layer 507 to be compressed. A non-compressed-region 603, in which a first-spacing 604 between adjacent conductive particles is illustrated. A compressed-region 605 is also illustrated. In this compressed region, a second-spacing 606, between adjacent conductive particles, is significantly smaller than the first-spacing 604 between non-compressed particles. Thus, given that the density of the carbon particles in the compressed-region 605 has increased compared to the density of the carbon particles in non-compressed-region 603, the regions will influence an applied electric field differently. In this way, a response to the mechanical-interaction 601 is enhanced, thereby producing larger input signals. This in turn assists in terms distinguishing signals that are required over noise that may be inadvertently induced, thereby improving the signal-to-noise ratio.

FIG. 7

A method of constructing a mattress-based detection apparatus for a human or animal body will be described with reference to FIGS. 7 to 11. This involves establishing an electrically conductive ground-plane and configuring a laminated-membrane of a detector over this ground-plane. A response-enhancement-layer is deployed upon the laminated-membrane, that is constructed from a substantially non-conducting compressible-material containing electrically-conductive-particles. Thereafter, an upper-mattress is arranged over the response-enhancement-layer.

Figure 7:
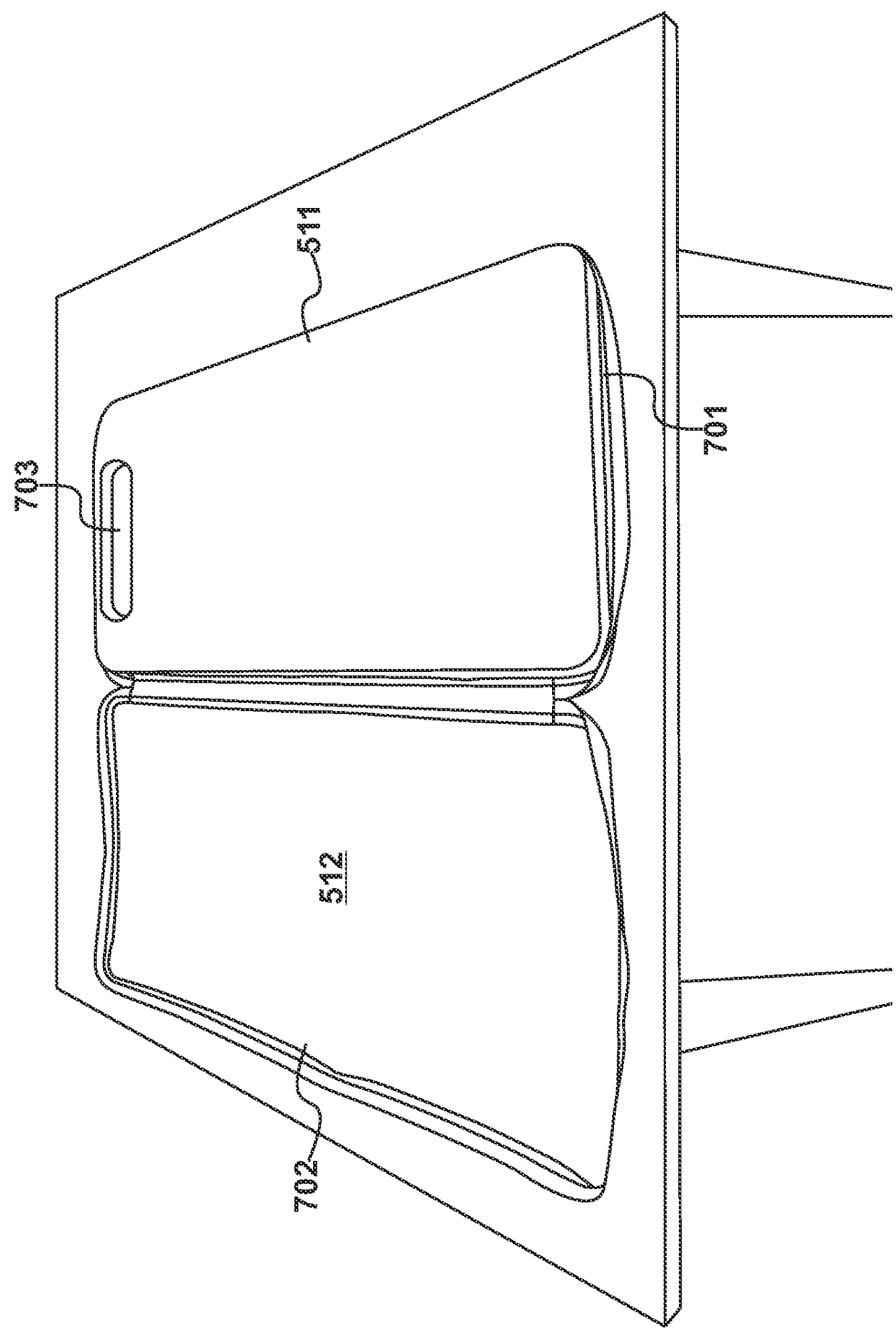
FIG. 7 shows a lower-mattress placed over a lower-section of a cover.
Figure 8:
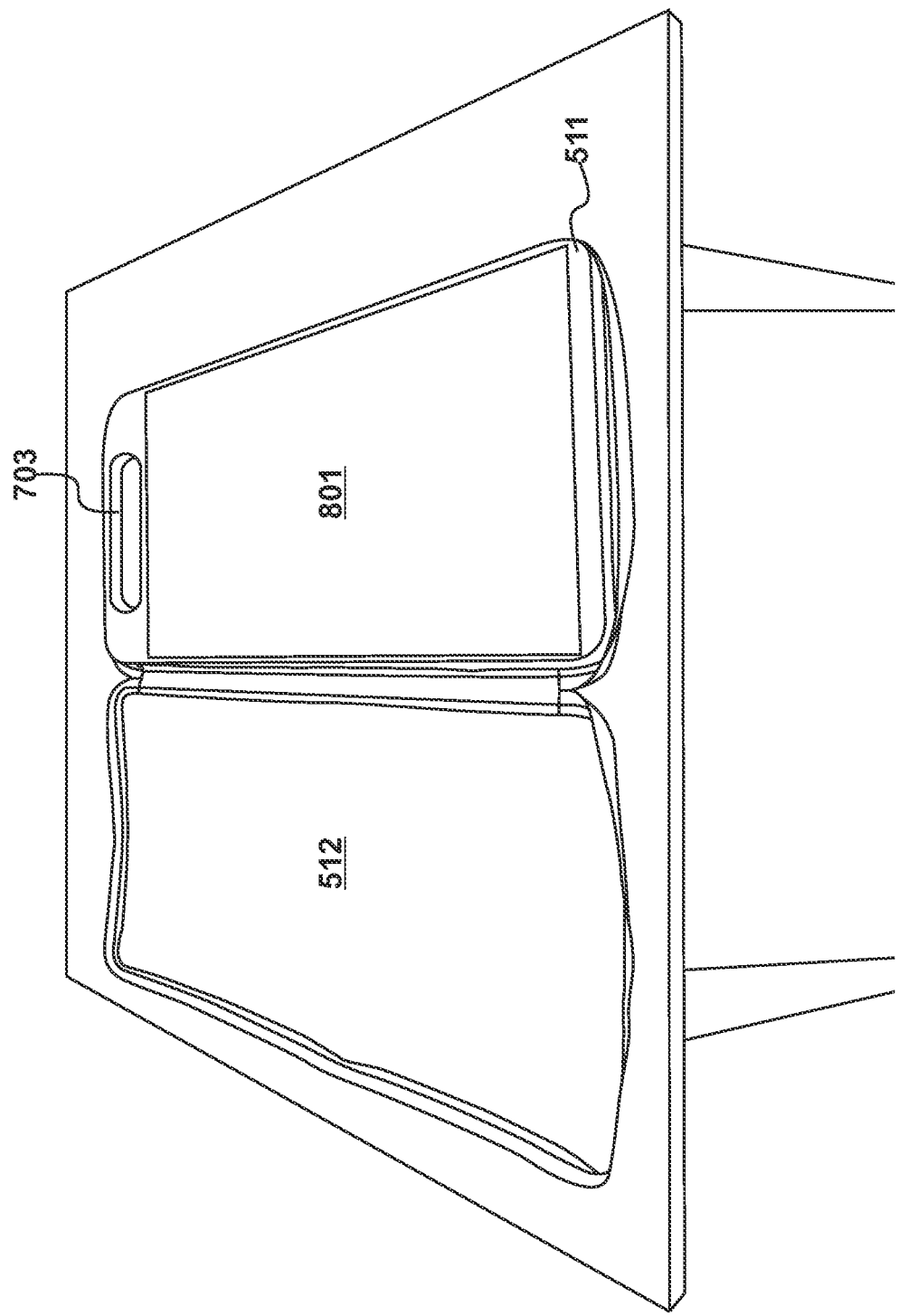
FIG. 8 shows a ground-plane being arranged upon the lower-mattress identified in FIG. 5.

In FIG. 7, a lower-mattress 511 has been placed over a lower-section 701 of the cover 512 that also includes an upper-section 702. In this embodiment, the lower-section 701 of the cover also includes a cut-out 703 for receiving a control-circuit.

FIG. 8

After placing the lower-mattress 511 upon the lower-section 701, a ground-plane 801 is arranged upon the lower-mattress 511. As illustrated in FIG. 5, the ground-plane 801 covers substantially all of the lower-mattress 511, with the exception of the area containing the cut-out 703.

FIG. 9

Figure 9:
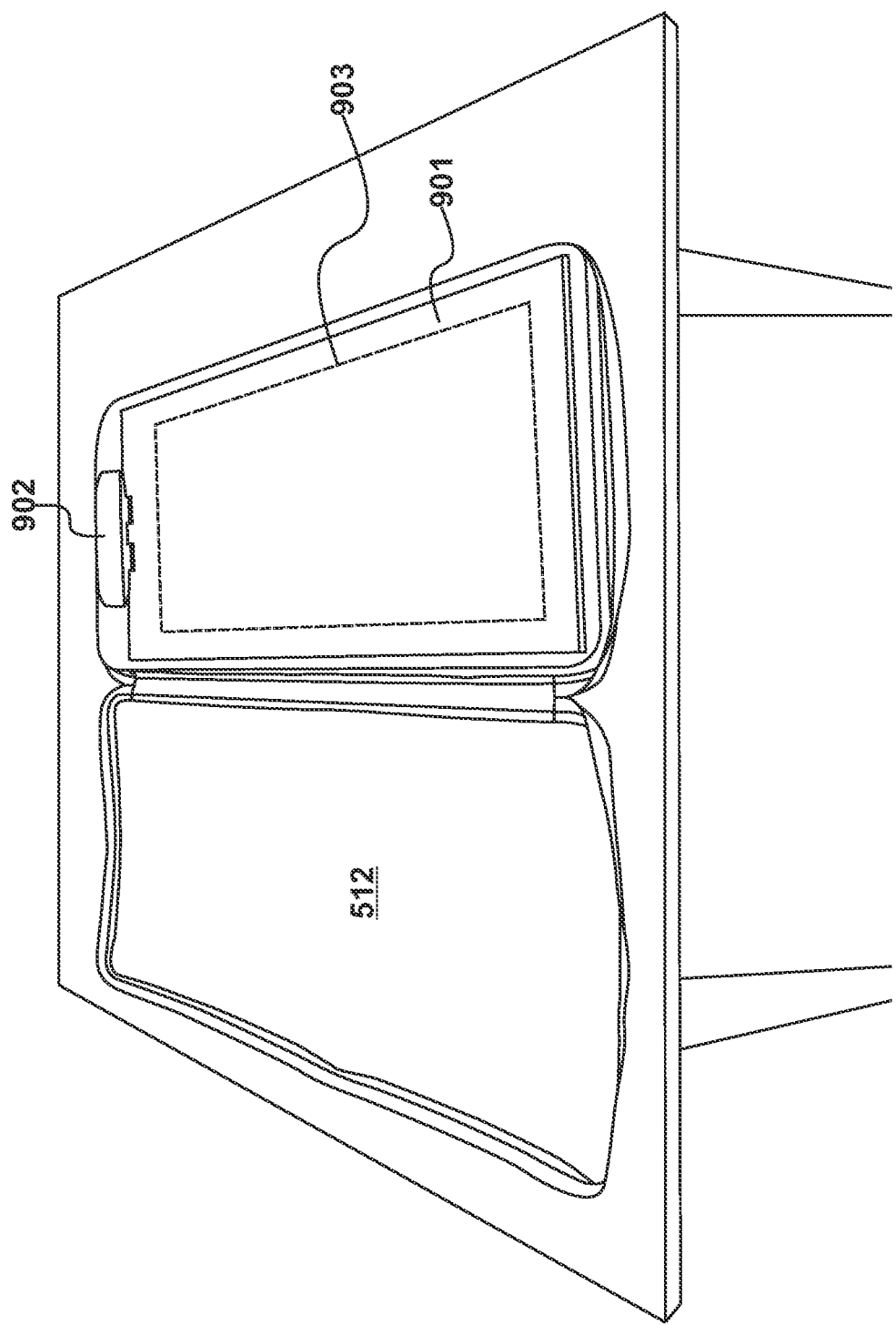
FIG. 9 shows the deployment of a detector-subassembly over the ground-plane identified in FIG. 8.

In an embodiment, as illustrated in FIG. 9, a detector-subassembly 901 is deployed over the ground-plane 801. A laminated-membrane, contained within the detector-subassembly 601, is connected to a control-circuit 902. The control-circuit 902 is then restrained within the cut-out 703.

An upper-mattress is arranged over the detector-subassembly, such that this upper-mattress is arranged over the response-enhancement-layer. In this embodiment, the upper-mattress is substantially similar to the lower-mattress and further encases the control-circuit 902. The upper-cover section 702 is then folded over and the whole apparatus secured by an appropriate mechanism, such as a zip fastener.

Additional stitching 903 may be deployed to further secure the detector-subassembly.

FIG. 10

The detector-subassembly 901 is assembled from the secondary-neoprene-composite-layer 508, the laminated-membrane 502 and the primary-neoprene-composite-layer 507. As illustrated in FIG. 7, a laminated-membrane 1001 has been placed over a secondary-neoprene-composite-layer 1002. This ensures that the secondary-neoprene-composite-layer 508, during assembly, is positioned between the ground-plane 801 and the laminated-membrane 1001.

As illustrated in FIG. 7, a paper-backing-material 1003 is removed from the laminated-membrane 1001, to reveal an adhesive that is used to secure the laminated-membrane 1001 to a primary-neoprene-composite-layer. Thus, the presence of adhesive on both surfaces of the laminated-membrane ensures that the response-enhancement-layer and the secondary-compressible-layer are secured to the laminated-membrane in order to form the detector-subassembly 601.

FIG. 11

Figure 10:
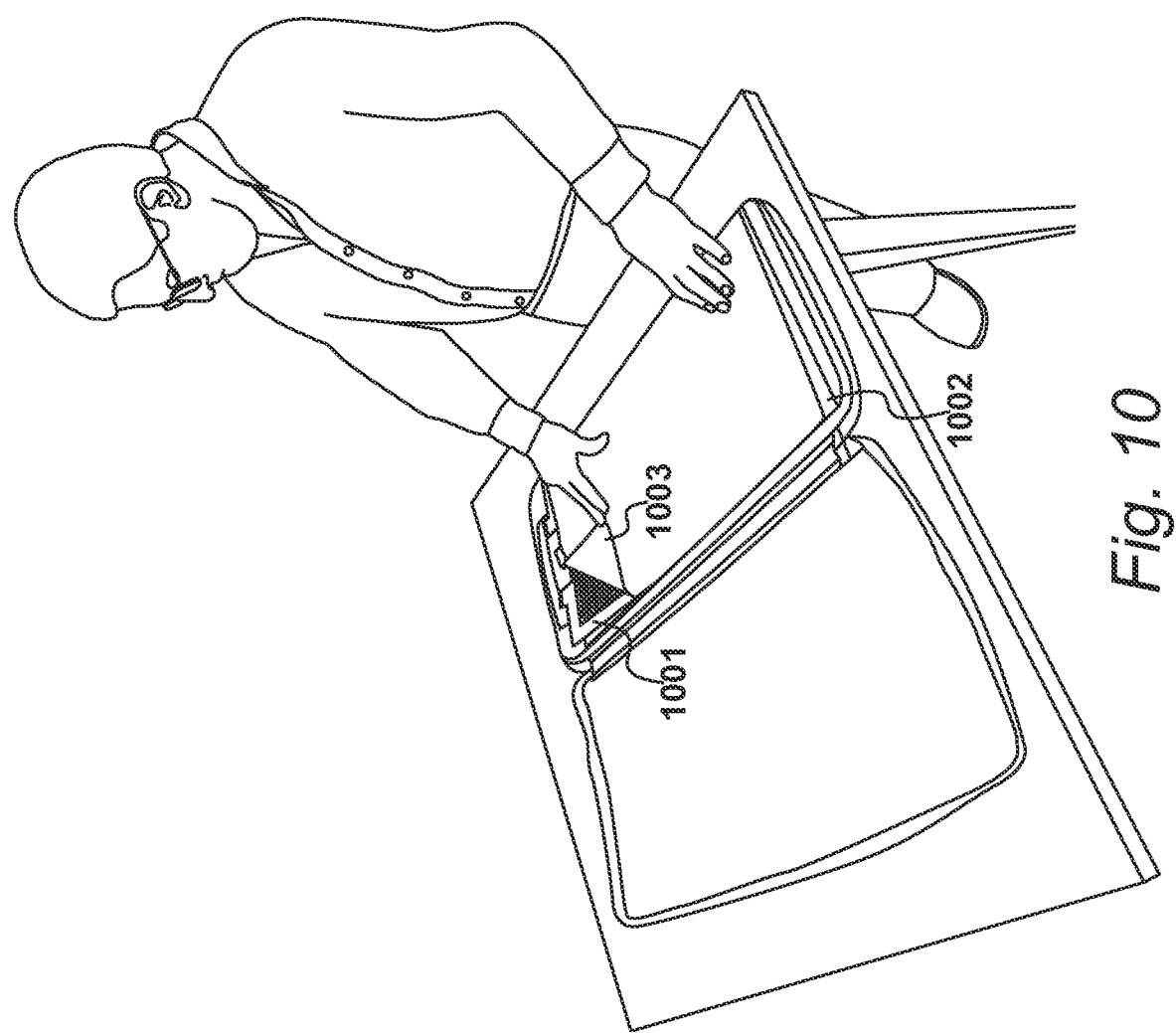
FIG. 10 illustrates a laminated-membrane being placed over a secondary-neoprene-composite-layer.
Figure 11:
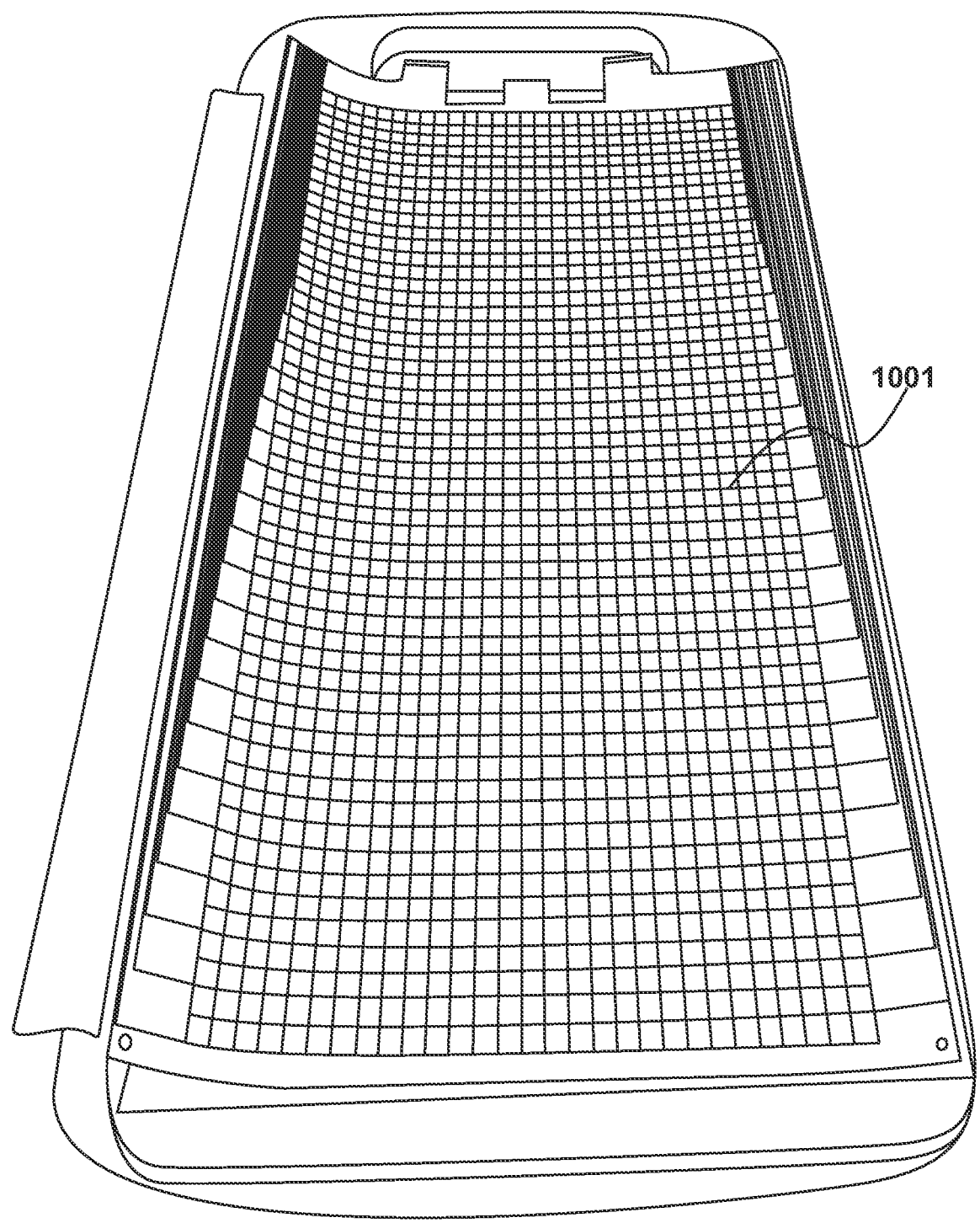
FIG. 11 illustrates a laminated-membrane after the removal of backing paper.

The laminated-membrane 1001 of FIG. 10 is illustrated in FIG. 11, after the removal of the paper-backing-material 1003. The laminated-membrane 1001 is now ready to receive the primary-neoprene-composite-layer 207, which in turn contains the response-enhancement-layer 504. During subsequent fabrication, an upper-mattress 503 is applied, as previously described.

FIG. 12

Figure 12:
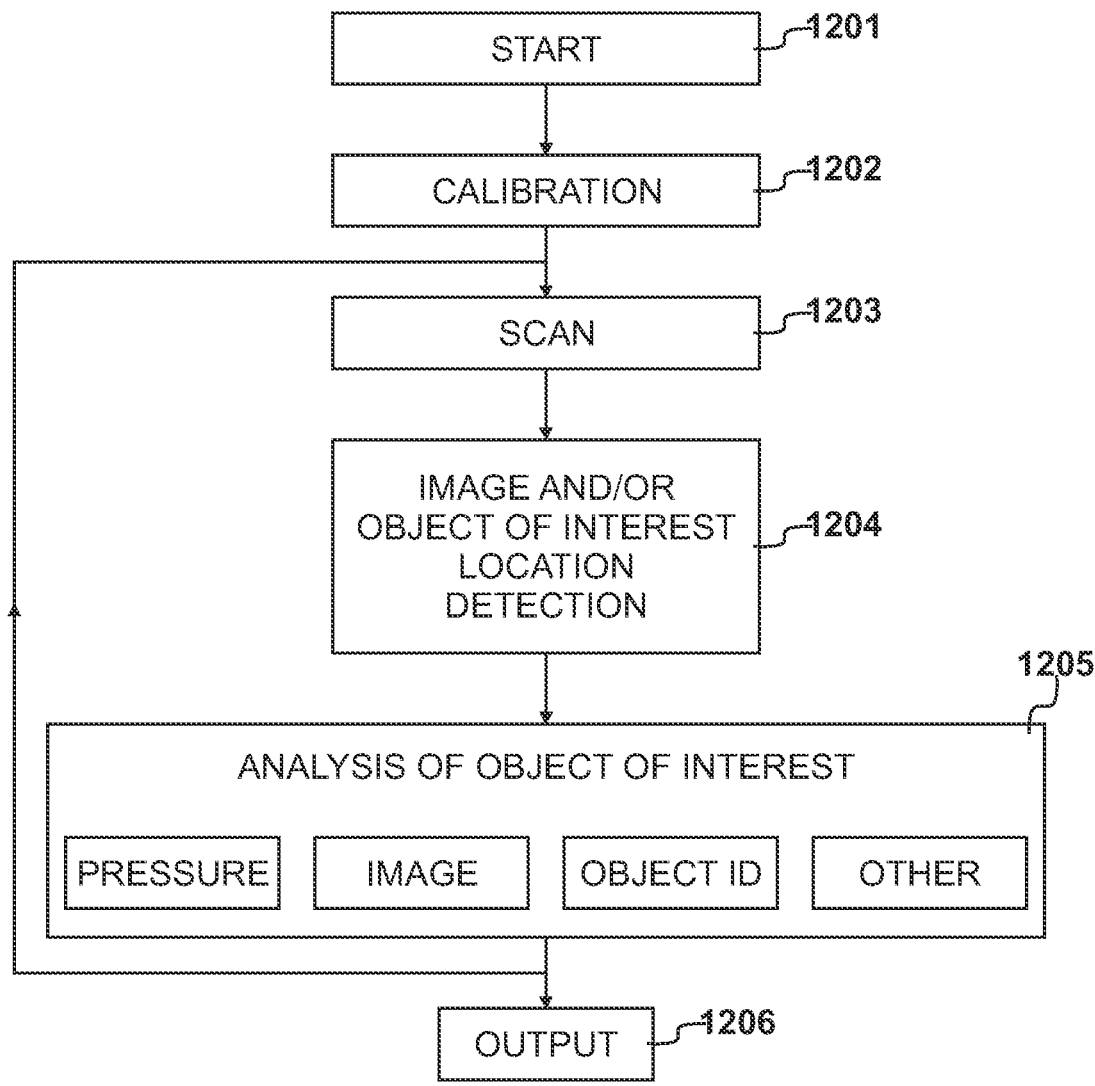
FIG. 12 illustrates procedures carried out to analyse an object.

Procedures carried out to analyse an object that is placed on the mattress-based detection apparatus are illustrated in FIG. 12. At step 1201, the sensor is switched on and is then calibrated at step 1202. The calibration is carried out without any test object and produces reference values for capacitive coupling between tracks. The calibration also has the benefit of negating any effect of temperature and humidity, which are capable of affecting the strength of received signals. During this step, the received voltage is measured. Alternatively, the calibration may be carried out with a reference test object.

When an object is placed on or over the sensor, a scanning step 1203 is carried out, where an input voltage is applied to each transmit track and a received voltage on each receive track is measured. At step 1204, the measured values from the calibration step 1202 and scanning step 1203 are analysed and an image of the object is generated. From the generated image, the location of a specific object of interest is determined.

At step 1205, the specific object of interest is analysed and the sensor is able to use a training algorithm that is specific to the application of interest in order to identify the object, generate a pressure map and/or generate a visual image of the object to interest. This is done by comparing the measured capacitive coupling against a data set of capacitive couplings mapped to different materials or combination of materials.

A number of training learning algorithms may be used in this identification stage, for example machine learning algorithms such as, but not limited to; decision tree learning, association rule learning, support vector machines and/or artificial neural networks.

Following step 1205, the sensor may be scanned again at step 1202, or analysed data may be supplied at an output step 1206.

FIG. 13

Figure 13:
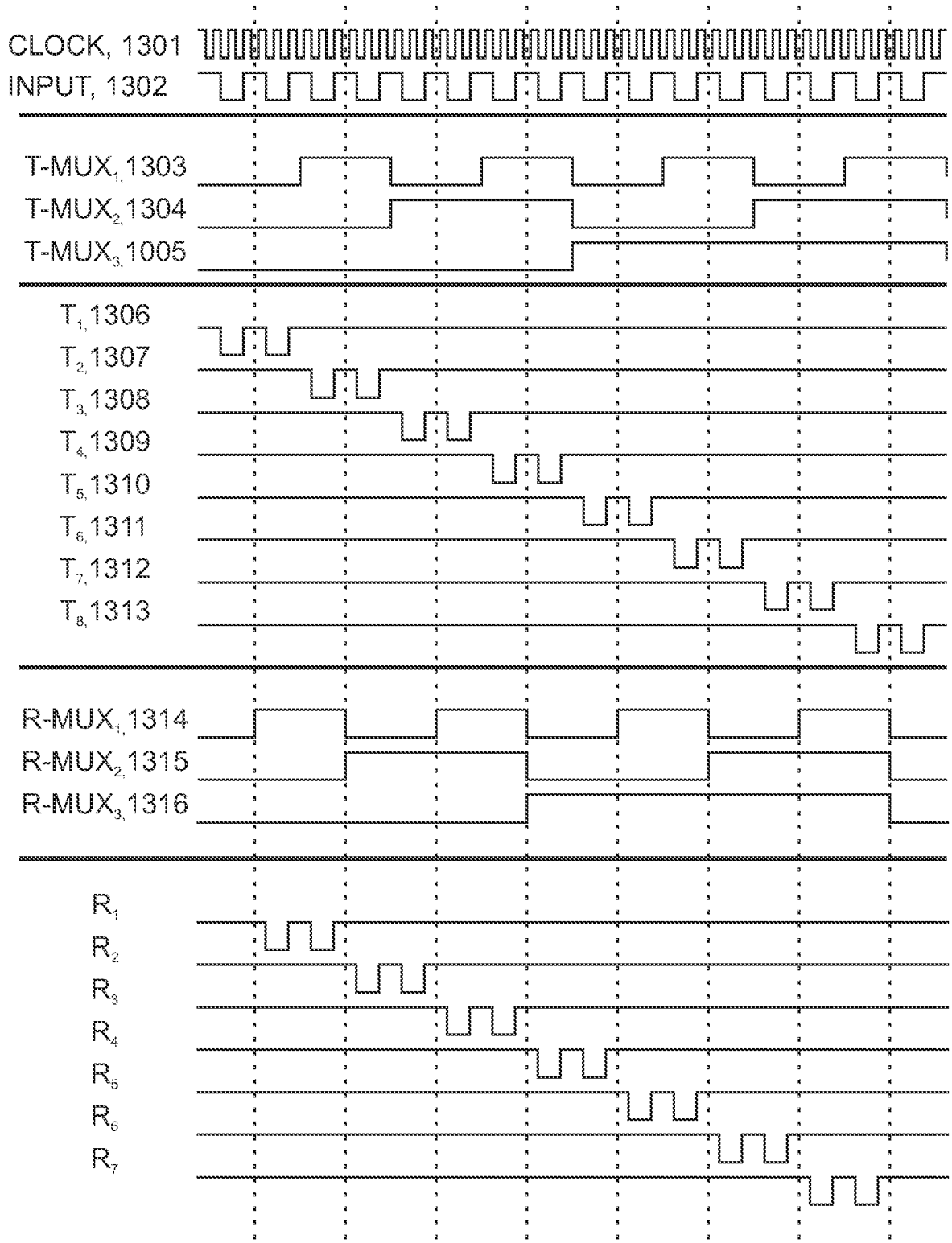
FIG. 13 shows an example of a timing diagram for scanning transmit and receive electrodes.

An example timing diagram for scanning transmit and receive electrodes in a sensor array is shown FIG. 13. A clock signal 1301 provides a main reference signal and in this example, the clock frequency is ten megahertz, but in other embodiments the clock frequency may be higher or lower depending upon the resolution required.

At 1302, an input signal produced by signal generator 204 is illustrated and has a frequency of repetition of $2f$, where $f$, derived from the clock signal, has a frequency of one kilohertz. Signal generator 204 therefore produces input signals at a repetition frequency of two kilohertz. The transmitter multiplexer 203 is configured to multiplex input signals from signal generator 204 across each transmitter electrode in the sensor array 201. For this purpose, it includes three switching channels, which are controlled by signals illustrated at 1303, 1304 and 1305. By altering the switching of each channel, it is possible to multiplex input signals across eight channels. The transmitter multiplexer is therefore configured to switch between its outputs in sequence and at a frequency $f$, which, in keeping with this example, would be a frequency of one kilohertz. As shown at 1306 to 1313, this results in two pulses being applied to each transmitter electrode.

The switching of channels in the receiver multiplexer, to multiplex output signals from each receiver electrode into signal detector 1006, is shown at 1314, 1315 and 1316. The receiver multiplexer is configured to switch between input channels in sequence at a frequency $f$ (one kilohertz). However, the switching of inputs occurs one-hundred-and-eighty degrees out of phase with the switching in transmitter multiplexer 203 and so results in two output signals from each receiver electrode being provided to the signal detector. In this way, an output signal is derived from a signal transmitted from a transmit electrode to one side of the receive electrode and a second output signal is derived from the signal transmitted from a transmit electrode to another side of the receive electrode.

In effect, therefore, each receiver electrode "listens" for capacitive coupling from a transmitter electrode to its left and then a transmitter electrode to its right. This allows the recording of two measurements of the degree of capacitive coupling per receiver electrode. In an embodiment, processing then takes place on the two measurements to effect linear interpolation. More measurements allow processing to take palace to effect polynomial interpolation, resulting in more accurate data sets for analysis.

Clearly, in the example shown in the Figures, there are only seven receiver electrodes, and so one of the inputs of the demultiplexer 205 will be connected to ground, such that the measuring device receives zero input when the corresponding channel is selected.

FIG. 14

Figure 14:
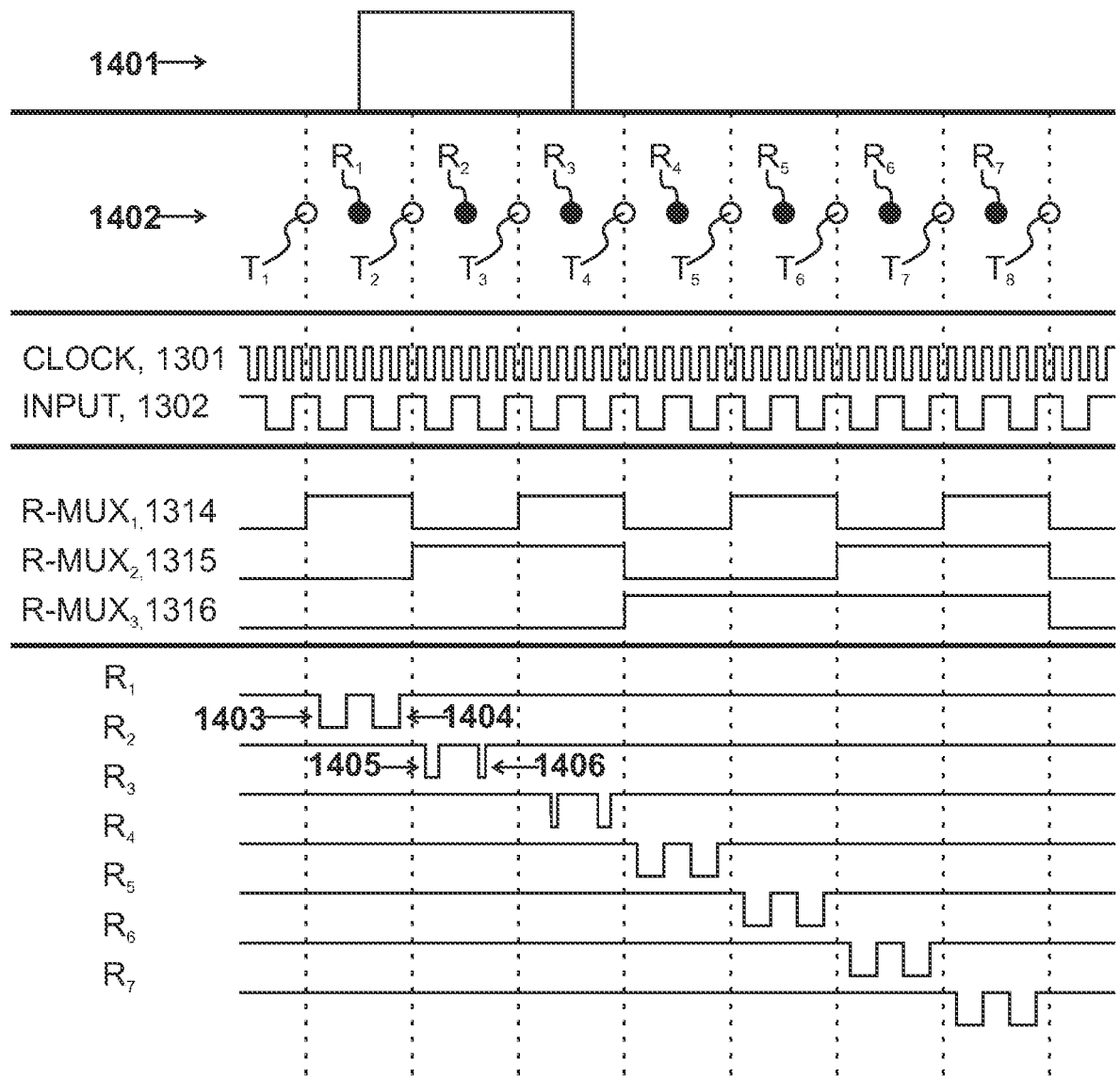
FIG. 14 shows example signals provided to the signal detector.

Example signals provided to the signal-detector 206, when an object is placed on the sensor array 201, are shown in FIG. 14. The object placed on the sensor array is shown at 1401, with an arrangement of transmit electrodes ($T_1$ to $T_8$) and receive electrodes ($R_1$ to $R_7$) as illustrated at 1402.

At 1301, the clock signal is illustrated, again running at a frequency of ten megahertz. Input signals shown at 1302 are produced at a repetition frequency of ten kilohertz and multiplexed across the transmitter electrodes as previously described. The switching of inputs in demultiplexer 205 results in all of the signals formed on the receiver electrodes being provided to signal detector 206. For ease of illustration, the output signals produced by the signal detector are shown for the respective receiver electrode that they originated from and are labelled $R_1$ to $R_7$.

When considering $R_1$, the output signal produced when an input signal is applied to transmitter electrode $T_1$ is shown at 1403, and the output signal produced when an input signal is applied to transmitter electrode $T_2$ is shown at 1404. If there is no part of the object present between $T_1$ and $R_1$, there is no change to the electric field between $T_1$ and $R_1$ and so the width of measurement signal 1403 is not changed. If there is indeed part of the object present between $R_1$ and $T_2$, there is a reduction in the width of the measurement signal and the difference between these signals is illustrated at 1405 and 1406; where there is a clear decrease in the width of the measurement due to reduction of the capacitive coupling between $T_2$ and $R_2$, and $T_3$ and $R_2$.

In this embodiment, as the frequency of switching of the multiplexers happens at eight kilohertz, a total scan of the array occurs at a frequency of one kilohertz. The duration of each of the output signals proceeded by a signal detector in a single scan is compared with the clock signal to produce duration data corresponding to the positions, which may then be provided to the data-processing-system 102.

FIG. 15

Figure 15:
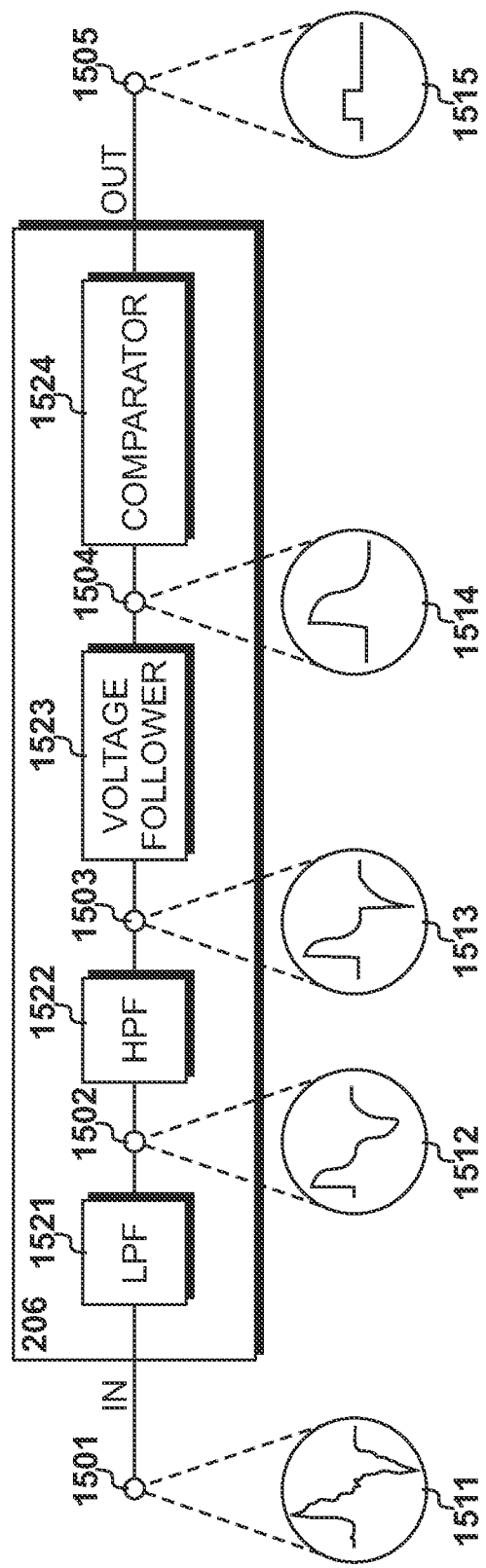
FIG. 15 shows an example of a signal detector.

An example of a signal-detector 206, as previously described with reference to FIG. 2, is shown in FIG. 15, used in accordance with an aspect of the present invention. Signal detector 206 is arranged to receive at an input terminal a signal from demultiplexer 205 and to output a sample signal indicative of the voltage in a receiver electrode.

The signal produced in a receiver electrode is a voltage that peaks and decays in a positive sense when an increase in voltage is applied to a neighbouring transmitter electrode; and peaks and decays in a negative sense when a decrease in voltage is supplied to a neighbouring electrode. This is due to the changes in the strength of the electric field between the transmit and receive electrodes, which in turn results in the manifestation of a voltage on the receiver electrode.

The signal-detector 206 includes an input terminal 1501, at which an example-signal 1511 is shown. Example-signal 1511 is conditioned by a low pass filter 1521 which filters out high frequency components of the signal to give a first filtered signal 1212. The first filtered signal 1512 is then provided to an input 1502 of a high pass filter 1522 that filters out low frequency components. This filtering gives a second filtered signal 1513 that is provided to one input of a voltage follower 1523, which is configured to output a signal 1514 representing only the positive portion of second filtered signal 1512.

Alternatively, the input signal may also go through a band pass filter to provide one input 1503 to the voltage follower 1523. The voltage follower 15233 has an extremely high input impedance and a very low output impedance and thus serves to avoid crosstalk between the two sides of the signal detector 206. The output from voltage follower 1523 is provided to an input 1504 of a comparator 1524 which is configured to compare signal 1514 to a threshold voltage.

This comparison process produces a signal at an output 1505 having a pulse 1515 with a width in the time domain that is proportional to the extent to which signal 1214 exceeds the threshold voltage. Given identical input signals on a neighbouring transmitter electrode, the response of a receive electrode is always similar in profile. However, the amplitude of the output signal changes based upon the level of capacitive coupling present. The duration of comparison signal 1215 is therefore proportional to the amplitude of the voltage developed at the receiver electrode and in turn the capacitive coupling between the transmitter and receiver electrode providing the input to the signal detector.

The comparison signals produced by the signal-detector 206 are sampled by timing their durations. The durations are stored in memory as duration data for further analysis, which can include the application of algorithms that effect interpolation of the data.

FIG. 16

Figure 16:
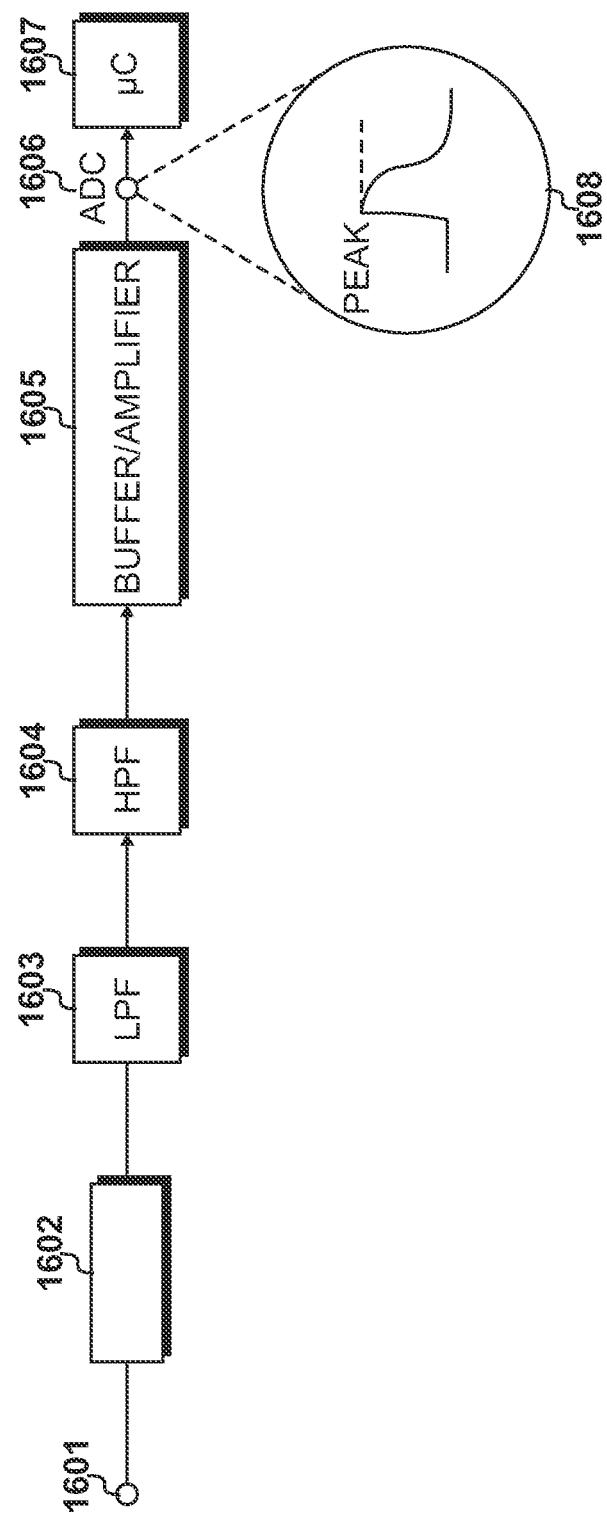
FIG. 16 shows an alternative example of a signal detector.

An alternative embodiment for a signal detector is shown diagrammatically in FIG. 16. The alternative signal detector 206 is arranged to receive at an input terminal a signal from demultiplexer 205 and to produce an output indicative of the voltage of a receive electrode. The input signal received by a receive track 1601 when an object is placed on top of the sensor is measured. At 1602, the measured reference voltage during calibration, as described above, is taken into account in order to eliminate unwanted noise and the voltage signal is calculated as the difference between the reference voltage and the object voltage. This difference value is then transmitted to a low pass filter 1603 that filters out high frequency components of the signal. The filtered signal is then sent through a high pass filter 1604 that filters out low frequency components of the filtered signal. This second filtered signal is then provided to the input of a buffer amplifier 1605, which is used to amplify and transform the second filtered signal.

The amplified signal is then sent to an analogue-to-digital convertor input 1606 of a microcontroller 1607. The amplitude or peak of the signal (as indicated at 1608) varies, depending upon the amount of capacitive coupling received. The amplitudes are stored in memory for further analysis, which can include the application of algorithms that perform interpolation of the data to give a much higher resolution of the extracted results.

The invention claimed is:

1. An apparatus for detecting changes in pressure applied by a human or animal body upon a mattress, comprising:
    an electrically conductive ground-plane;
    a laminated-membrane having transmit electrodes and receive electrodes connected to a control-circuit; and
    an upper-mattress for supporting said human or animal body, wherein:
        said control-circuit is configured to energise selected ones of said transmit electrodes and monitor selected ones of said receive electrodes, such that an electric field generated by said selected ones of said transmit electrodes passes through said upper-mattress and is detected by at least some of said selected ones of said receive electrodes,
        a response-enhancement-layer of a substantially electrically non-conducting compressible-material containing electrically-conductive-particles is located between said laminated-membrane and said upper-mattress, and
        a density of said electrically-conductive-particles increases with said pressure applied by said human or animal body thereby enhancing changes to said electric field.

2. The apparatus of claim 1, wherein said electrically-conductive-particles are particles of carbon.

3. The apparatus of claim 1, wherein said substantially electrically non-conducting compressible-material is an expanded foam-based material.

4. The apparatus of claim 3, wherein said substantially electrically non-conducting compressible-material is neoprene, said electrically-conductive-particles are particles of carbon, and said particles of carbon are dispersed in a first-neoprene-layer.

5. The apparatus of claim 4, wherein a second layer of a compressible-material that does not contain electrically-conductive-particles is positioned between said laminated-membrane and said first-neoprene-layer.

6. The apparatus of claim 5, wherein said second layer is a second-neoprene-layer.

7. The apparatus of claim 6, wherein said second-neoprene-layer is attached to said first-neoprene-layer as a primary-neoprene-composite-layer.

8. The apparatus of claim 7, wherein:
    a secondary-neoprene-composite-layer is located between said electrically conductive ground-plane and said laminated-membrane;
    said secondary-neoprene-composite-layer comprises a third-layer that contains electrically-conductive-particles attached to a fourth-layer that does not contain electrically-conductive-particles;
    said third-layer containing electrically-conductive-particles is placed in contact with said electrically conductive ground-plane; and said fourth-layer is placed in contact with said laminated-membrane.

9. The apparatus of claim 8, wherein said primary-neoprene-composite-layer and said secondary-neoprene-composite-layer are both secured to said laminated-membrane to form a detector-subassembly.

10. The apparatus of claim 1, further comprising a lower-mattress for supporting said electrically conductive ground-plane.

11. A method of constructing a mattress-based pressure-detection-device for a human or animal body, comprising the steps of:
  establishing an electrically conductive ground-plane; and
  configuring a laminated-membrane of a detector over said electrically conductive ground-plane, having a plurality of transmit electrodes for generating electric fields and a plurality of receive electrodes for detecting said electric fields;
  deploying a response-enhancement-layer upon said laminated-membrane, wherein said response-enhancement-layer is constructed from a substantially electrically non-conducting compressible-material containing electrically-conductive-particles; and
  arranging an upper-mattress over said response-enhancement-layer, wherein:
    said electric fields pass through said response-enhancement-layer and said upper-mattress; and
    detection of pressure due to said human or animal body is enhanced by said response-enhancement-layer, due to a density of said electrically-conductive-particles increasing with increasing applied pressure.

12. The method of claim 11, further comprising the step of arranging said electrically conductive ground-plane upon a lower-mattress.

13. The method of claim 11, wherein a secondary-compressible-layer is positioned between said electrically conductive ground-plane and said laminated-membrane.

14. The method of claim 13, wherein said deploying step includes the step of securing said response-enhancement-layer and said secondary-compressible-layer to said laminated-membrane to form a detector-subassembly.

15. The method of claim 11, further comprising the step of connecting a control-circuit to said laminated-membrane.

* * * * *